United States Patent [19]

Chen

[11] Patent Number: 5,635,531
[45] Date of Patent: Jun. 3, 1997

[54] 3'-AMINOCARBONYLOXY PACLITAXELS

[75] Inventor: Shu-Hui Chen, Hamden, Conn.

[73] Assignee: Bristol-Myers Squibb Company, Princeton, N.J.

[21] Appl. No.: 679,415

[22] Filed: Jul. 8, 1996

[51] Int. Cl.$^6$ .................... A61K 31/335; A61K 31/34; A61K 31/38; C07D 405/02
[52] U.S. Cl. .................... 514/471; 514/63; 514/444; 514/449; 549/4; 549/60; 549/214; 549/472; 549/473; 549/510
[58] Field of Search .................... 549/510, 214, 549/472, 473, 60, 4; 514/449, 63, 471, 444

[56] References Cited

U.S. PATENT DOCUMENTS

| | | | |
|---|---|---|---|
| 4,814,470 | 3/1989 | Colin et al. | 514/449 |
| 4,942,184 | 7/1990 | Haugwitz et al. | 514/449 |
| 4,960,790 | 10/1990 | Stella et al. | 514/449 |
| 5,059,699 | 10/1991 | Kingston et al. | 549/411 |
| 5,227,400 | 7/1993 | Holton et al. | 514/444 |
| 5,229,526 | 7/1993 | Holton | 549/213 |
| 5,254,580 | 10/1993 | Chen et al. | 514/449 |
| 5,272,171 | 12/1993 | Ueda et al. | 514/449 |
| 5,283,253 | 2/1994 | Holton et al. | 514/444 |
| 5,294,637 | 3/1994 | Chen et al. | 514/449 |
| 5,319,112 | 6/1994 | Kingston et al. | 549/510 |
| 5,338,872 | 8/1994 | Holton et al. | 549/510 |
| 5,352,806 | 10/1994 | Gunawardana et al. | 549/510 |
| 5,395,850 | 3/1995 | Roth | 514/471 |
| 5,466,834 | 11/1995 | Holton | 549/510 |
| 5,468,769 | 11/1995 | Klein et al. | 514/449 |
| 5,478,854 | 12/1995 | Farina et al. | 514/374 |
| 5,489,589 | 2/1996 | Wittman et al. | 514/232.8 |
| 5,489,601 | 2/1996 | Holton et al. | 514/337 |
| 5,539,103 | 7/1996 | Holton | 540/354 |

FOREIGN PATENT DOCUMENTS

| | | |
|---|---|---|
| 400971A2 | 12/1990 | European Pat. Off. |
| 552041A2 | 7/1993 | European Pat. Off. |
| 558959A1 | 9/1993 | European Pat. Off. |
| 582469A2 | 2/1994 | European Pat. Off. |
| 590267A2 | 4/1994 | European Pat. Off. |
| 600517A1 | 6/1994 | European Pat. Off. |
| 604910A1 | 7/1994 | European Pat. Off. |
| 617034A1 | 9/1994 | European Pat. Off. |
| 634492A1 | 1/1995 | European Pat. Off. |
| WO93/06093 | 4/1993 | WIPO |
| WO94/08984 | 4/1994 | WIPO |
| WO94/14787 | 7/1994 | WIPO |
| WO94/13655 | 8/1994 | WIPO |
| WO94/17050 | 8/1994 | WIPO |
| WO94/20485 | 9/1994 | WIPO |

OTHER PUBLICATIONS

E.K. Rowinsky and R.C. Donehower, "The Clinical Pharmacology and Use of Antimicrotubule Agents in Cancer Chemotherapeutics," Pharmac. Ther., 52:35–84, 1991.

C.M. Spencer and D. Faulds, "Paclitaxel, A Review of its Pharmacodynamic and Pharmacokinetic Properties and Therapeutic Potential in the Treatment of Cancer," Drugs, 48(5), 794–847, 1994.

K.C. Nicolaou, et al., "Chemistry and Biology of Taxol," Angew. Chem., Int. Ed. Engl., 33:15–44, 1994.

Greene and Wuts, Protective Groups in Organic Synthesis, 2nd Ed., John Wiley & Sons, and McOmie, 1991.

Protective Groups in Organic Chemistry, Ed. J.F.W. McOmie, Plenum Press, 1973.

I. Ojima, et al. "New and Efficient Approaches to the Semi–Synthesis of Taxol and its C–13 Side Chain Analogs by Means of β–Lactam Synthon Method," Tetrahedron Letters, 48(34), 6985–7012, 1992.

I. Ojima, et al., "A Highly Efficient Route to Taxotere by the β–Lactam Synthon Method," Tetrahedron Letters, 34(26), 4149–4152, 1993.

R. Brieva, et al, J. Org. Chem., 58, 1068–1075, 1993.

S.–H. Chen, et al, "First Syntheses of Novel Paclitaxel (Taxol) Analogs Modified at the C4–Position," J. Org. Chem., 59, pp. 6156–6158, 1994.

S.–H. Chen, et al, "Structure–Activity Relationships of Taxol: Synthesis and Biological Evaluation of C2 Taxol Analogs," Bioorganic and Medicinal Chemistry Letters, vol. 4, No. 3, pp. 479–482, 1994.

R.A. Johnson, "Taxol Chemistry. 7-O-Triflates as Precursors to Olefins and Cyclopropanes," Tetrahedron Letters, vol. 35, No. 43, pp. 7893–7896, 1994.

X. Liang and G.I. Kingston, "Synthesis and Biological Evaluation of Paclitaxel Analogs Modified in Ring C," Tetrahedron Letters, vol. 36, No. 17, pp. 2901–2904, 1995.

G. Roth, et al, "Reaction of Paclitaxel and 10–Desacetyl Baccatin III with Diehylamino Sulfurtrifluoride," Tetrahedron Letters, vol. 36, No. 10, pp. 1609–1612, 1995.

S.–H. Chen, et al, "The Chemistry of Taxanes: Reaction of Taxol and Baccatin Derivatives with Lewis Acids in Aprotic and Protic Media," Tetrahedron Letters, vol. 49, No. 14, pp. 2805–2828, 1993.

L.L. Klein, "Synthesis of 9–Dihydrotaxol: A Novel Bioactive Taxane," Tetrahedron Letters, vol. 34, No. 13, pp. 2047–2050, 1993.

Physician's Desk Reference, 49th Edition, Medical Economics, p. 682, 1995.

N. Gerber, et al, "Safety, Tolerance and Pharmacokinetics of Intravenous Doses of the Phosphate Ester of 3–Hydroxymethyl–5,5–Diphenylhydantoin: A New Prodrug of Phenytoin," J. Clin. Pharmacol., 28, pp. 1023–1032, 1988.

(List continued on next page.)

Primary Examiner—Joseph K. McKane
Attorney, Agent, or Firm—William T. Han; Samuel J. DuBoff

[57] ABSTRACT

The present invention concerns novel paclitaxel derivatives, their use as antitumor agents, and pharmaceutical formulations.

15 Claims, No Drawings

OTHER PUBLICATIONS

J. Kant, et al, "A Chemoselective Approach to Functionalize the C–10 Position of 10–Deacetylbaccatin III. Synthesis and Biological Properties of Novel C–10 Taxel Analogues," Tetrahedron Letters, 35, No. 31, pp. 5543–5546, 1994.

A.S. Kearney and V.J. Stella, "Hydrolysis of Pharmaceutically Relevant Phosphate Monoester Monoanions: Correlation to an Established Structure–Reactivity Relationship," J. of Pharmaceutical Sciences, 82, No. 1, pp. 69–72, Jan., 1993.

A.M.P. Koskinen, et al, "Enantioselective Synthesis of the Taxol and Taxotere Side Chains," J. Chem. Soc., Chem. Commun., pp. 21–22, 1994.

K.C. Nicolaou, et al, "design, Synthesis and Biological Activity of Protaxols," Nature, 364, No. 29, pp. 464–466, Jul., 1993.

M. Safadi, et al, "Phosphoryloxymethyl Carbamates and Carbonates—Novel Water–Soluble Prodrugs for Amines and Hindered Alcohols," Pharmaceutical Research, 10, No. 9, pp. 1350–1355, 1993.

D.M. Vyas, et al, "Synthesis and Antitumor Evaluation of Water Soluble Taxol Phosphates," Bioorganic & Medicinal Chemistry Letters, 3, No. 6, pp. 1357–1360, 1993.

D.M. Vyas, et al, "Chapter 9. Phosphatase–Activated Prodrugs of Paclitaxel," Taxane Anticancer Agents: Basic Science and Current Status, pp. 124–137, American Chemical Society, Washington, D.C., G.I. Georg, et al (ED), 1995.

Z.–M. Wang, et al, "Large–Scale and Highly Enantioselective Synthesis of the Taxol C–13 Side Chain through Asymmetric Dihydroxylaion," J. Org. Chem., 59, No. 17, pp. 5104–5105, 1994.

S.–H. Chen, et al, "Taxol® Structure–Activity Relationships: Synthesis and Biological Evaluation of Taxol Analogs Modified at C–7," Bioorganic & Medicinal Chemistry Letters, vol. 4, No. 18, pp. 2223–2228, 1994.

Mahendra D. Chordia, et al., "Synthesis and Biological Evaluation of 4–Deacetoxy–paclitaxel," Tetrahedron Letters, vol. 35, No. 37, pp. 6843–6846, 1994.

K.A. Neidigh, et al, "Synthesis and Biological Evaluation of 4–Deacetyl–paclitaxel," Tetrahedron Letters, vol. 35, No. 37, pp. 6839–6842, 1994.

F.A. Holmes, et al, Taxane Anticancer Agents Basic Science and Current Status, edited by G.I. Georg, et al., 1995, American Chemical Society, Washington, D.C. 31–57.

S.G. Arbuck, et al, Taxol® Science and Applications, edited by M. Suffness, 1995 (R. C. Press Inc., Boca Raton, Florida), pp. 379–416.

J.W. Harris, et al, J. Med. Chem., 37, pp. 706–709, 1994.

A. Rahman, et al, Cancer Research, 54, pp. 5543–5546, 1994.

G. Kumar, et al, Cancer Chemother. Pharmacol., 36, pp. 129–135, 1995.

J.–N. Denis, et al, "Docetaxel (Taxotere) Derivatives: Novel $NbCl_3$–Based Stereoselective Approach to 2'–Methyldocetaxel," J. Chem. Soc. Perkin Trans. 1, pp. 1811–1815, 1995.

F. Gueritte–Voegelein, et al, "Chemical Studies of 10–Deacetyl Baccatin III. Hemisynthesis of Taxol Derivatives," Tetrahedron Letters, vol. 42, No. 16, pp. 4451–4460, 1986.

K. C. Nicolaou, et al, "Chemical Synthesis and Biological Evaluation of C–2 Taxoids," J. Am. Chem. Soc., 117, pp. 2409–2420, 1995.

K. V. Rao, et al, "Synthesis and Evaluation of Some 10–Mono– and 2', 10–Diesters of 10–Deacetylpaclitaxel," J. Med. Chem., 38, pp. 3411–3414, 1995.

W. C. Rose, "Evaluation of Madison 109 Lung Carcinoma as a Model for Screening Antitumor Drugs," Cancer Treatment Reports, 65, No. 3–4, pp. 299–312, Mar.–Apr. 1981.

F. Gueritte–Voegelein, et al, "Relationships Between the Structure of Taxol Analogues and Their Antimitotic Activity," J. Med. Chem., 34, pp. 992–998, 1991.

C. S. Swindell, et al, "Biologically Active Taxol Analogues with Deleted A–Ring Side Chain Substituents and Variable C–2' Configurations", J. Med. Chem., 34, pp. 1176–1184, 1991.

H. J. Williams, et al, "NMR and Molecular Modeling Study of Active and Inactive Taxol Analogues in Aqueous and Nonaqueous Solution", Can. J. Chem., 72, pp. 252–260, 1994.

D. Guenard, et al, "Taxol and Taxotere: Discovery, Chemistry, and Structure–Activity Relationships", Acc. Chem. Res., 26, pp. 160–167, 1993.

L. Mangatal, et al, "Application of the Vicinal Oxyamination Reaction with Asymmetric Induction to the Hemisynthesis of Taxol and Analogues", Tetrahedron Letters, 45, (13), pp. 4177–4190, 1989.

J. Dubois, et al, "Conformation of Taxotere® and Analogues Determined by NMR Spectroscopy and Molecular Modeling Studies", Tetrahedron Letters, 49 (30), pp. 6533–6544, 1993.

3'-AMINOCARBONYLOXY PACLITAXELS

BACKGROUND OF THE INVENTION

1. Field of the Invention

The present invention concerns antitumor compounds. More particularly, the invention provides novel paclitaxel derivatives, pharmaceutical formulations thereof, and their use as antitumor agents.

2. Background Art

Taxol® (paclitaxel) is a natural product extracted from the bark of Pacific yew trees, *Taxus brevifolia*. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutics," *Pharmac. Ther.*, 52:35–84, 1991; by Spencer and Faulds in "Paclitaxel, A Review of its Pharmacodynamic and Pharmacokinetic Properties and Therapeutic Potential in the Treatment of Cancer," *Drugs*, 48 (5) 794–847, 1994; and by K. C. Nicolaou et al. in "Chemistry and Biology of Taxol," *Angew. Chem., Int. Ed. Engl.*, 33: 15–44, 1994, and also in the references cited therein.

A semi-synthetic analog of paclitaxel named Taxotere® (docetaxel) has also been found to have good antitumor activity. The structures of paclitaxel and Taxotere® are shown below along with the conventional numbering system for molecules belonging to the class; such numbering system is also employed in this application.

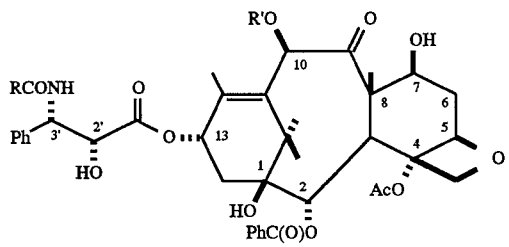

Taxol ®: R = Ph; R' = acetyl
Taxotere ®: R = t-butoxy; R' = hydrogen

SUMMARY OF THE INVENTION

This invention relates to novel antitumor compounds represented by formula I, or pharmaceutically acceptable salts thereof

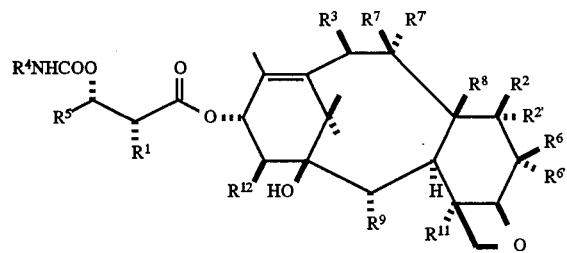

wherein $R^1$ hydroxy, —OC(O)$R^x$ or —OC(O)O$R^x$; $R^2$ is hydrogen, hydroxy, methoxy, —OC(O)$R^x$ or —OC(O)O$R^x$; $R^{2'}$ is hydrogen, hydroxy or fluoro; $R^{6'}$ is hydrogen or hydroxy; $R^6$ is hydrogen, or $R^2$ and $R^6$ together can form oxirane ring or a bond; $R^3$ is hydrogen, hydroxy, $C_{1-6}$alkyloxy, —OCONR$^{14}$R$^{15}$, —OC(O)$R^x$ or —OC(O)O$R^x$; $R^8$ is methyl or hydroxymethyl, or $R^8$ and $R^2$ together can form cyclopropane ring; $R^9$ is hydroxy or —OC(O)$R^x$; with the proviso that when $R^8$ and $R^2$ form cyclopropane ring, $R^{2'}$ is hydrogen; when $R^2$ and $R^6$ form oxirane ring or double bond, $R^{2'}$ and $R^{6'}$ are hydrogen; when $R^2$ is hydroxy, methoxy, —OC(O)$R^x$ or —OC(O)O$R^x$, $R^{2'}$ is hydrogen; when $R^{2'}$ is fluoro, $R^2$ is hydrogen; one of $R^7$ or $R^{7'}$ is hydrogen and the other is hydroxy, —OC(O)$R^x$ or —OC(O)O$R^x$, or $R^7$ and $R^{7'}$ together can form an oxo group; $R^{14}$ and $R^{15}$ are independently $C_{1-6}$ alkyl, hydrogen, aryl or substituted aryl; $R^4$ and $R^5$ are independently $C_{1-6}$ alkyl, $C_{2-6}$ alkenyl, $C_{2-6}$ alkynyl, or —Z—$R^{10}$; Z is a direct bond, $C_{1-6}$ alkyl or $C_{2-6}$ alkenyl; $R^{10}$ is aryl, substituted aryl, $C_{3-6}$ cycloalkyl or heteroaryl; $R^{11}$ is —OC(O)$R^y$ or —OC(O)O$R^y$; $R^{12}$ is hydrogen or hydroxy; $R^y$ is $C_{3-6}$ cycloalkyl or $C_{1-6}$ alkyl; $R^x$ is $C_{3-6}$ cycloalkyl, $C_{2-6}$ alkenyl or $C_{1-6}$ alkyl, all can be optionally substituted with one to six same or different halogen atoms; or $R^x$ is a radical of the formula

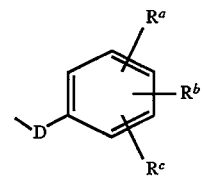

wherein D is a bond or $C_{1-6}$ alkyl; and $R^a$, $R^b$ and $R^c$ are independently hydrogen, nitro, cyano, azido, amino, $C_{1-6}$ alkylamino, di-$C_{1-6}$ alkylamino, halogen, $C_{1-6}$ alkyl, hydroxy or $C_{1-6}$ alkoxy.

Another aspect of the present invention provides a method for inhibiting tumor in a mammalian host which comprises administering to said mammalian host an antitumor effective amount of a compound of formula I.

Yet, another aspect of the present invention provides a pharmaceutical formulation which comprises an antitumor effective amount of a compound of formula I in combination with one or more pharmaceutically acceptable carriers, excipients, diluents or adjuvants.

DETAILED DESCRIPTION

In the application, unless otherwise specified explicitly or in context, the following definitions apply. The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl.

Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, cyano, azido, $C_{1-6}$ alkylamino, di-$C_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl.

Additional examples of hydroxy protecting groups may be found in standard reference works such as Greene and Wuts, *Protective Groups in Organic Synthesis*, 2d Ed., 1991, John Wiley & Sons, and McOmie; and *Protective Groups in Organic Chemistry*, 1975, Plenum Press.

The term "taxane" or "taxane core" refers to moieties with a framework of the structure:

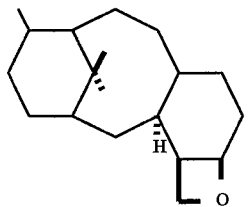

The cyclopropane group which can be constituted from $R^8$ and $R^2$ of formula I can alternatively be referred to as "7β,8β-methano" group as in Tetrahedron Letters, Vol 35, No 43, pp 7893–7896 (1994) or as "cyclopropa" group as in U.S. Pat. No. 5,254,580 issued Oct. 19, 1993. When $R^2$ and $R^6$ form a bond, naturally there will be a double bond between C7 and C6.

In compounds of formula I, examples of $R^x$ include methyl, ethyl, n-propyl, isopropyl, n-butyl, isobutyl, chloromethyl, 2,2,2-trichloroethyl, cyclopropyl, cyclobutyl, cyclopentyl, cyclohexyl, ethenyl, 2-propenyl, phenyl, benzyl, bromophenyl, 4-aminophenyl, 4-methylaminophenyl, 4-methylphenyl, 4-methoxyphenyl and the like. Examples of $R^4$ and $R^5$ include 2-propenyl, isobutenyl, 3-furanyl (3-furyl), 3-thienyl, phenyl, naphthyl, 4-hydroxyphenyl, 4-methoxyphenyl, 4-fluorophenyl, 4-trifluoromethylphenyl, methyl, ethyl, n-propyl, isopropyl, n-butyl, isobutyl, t-butyl, ethenyl, 2-propenyl, 2-propynyl, benzyl, phenethyl, phenylethenyl, 3,4-dimethoxyphenyl, 2-furanyl (2-furyl), 2-thienyl, 2-(2-furanyl)ethenyl, 2-methylpropyl, cyclopropyl, cyclobutyl, cyclopentyl, cyclohexyl, cyclohexylmethyl, cyclohexylethyl and the like.

The new products that have the general formula I display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by techniques from the conventional organic chemistry repertoire. Schemes I and II, which depict a process that compounds within the scope of formula I can be made, are only shown for the purpose of illustration and are not to be construed as limiting the processes to make the compounds by any other methods.

As shown in Scheme II, a compound of formula III can be employed to make a compound of this invention. Such compound of formula III can be made by a process of Scheme I, which is essentially the same process as described by F. Gueritte-Voegelein et al. in *Tetrahedron*, Vol. 42, No. 16, pp 4451–4460 (1986). Thus a compound of formula VII is coupled with an acrylic acid derivative of formula VIII to afford a compound of formula II which is subsequently oxidized to a diol of formula III. In Schemes I and II, $R^2$, $R^{2'}$, $R^3$, $R^4$, $R^5$, $R^6$, $R^{6'}$, $R^7$, $R^{7'}$, $R^8$, $R^9$, $R^{11}$, $R^{12}$ all have the meaning as previously defined; however, it is preferable that any reactive free hydroxy groups in a compound of formula VII be protected with hydroxy protecting groups until Step d of Scheme II at which stage they are removed.

In Scheme II, $R^{16}$ refers to a hydroxy protecting group, preferably triethylsilyl group. It is to be understood that hydroxy protecting group $R^{16}$ may be a carbonate or ester group —C(O)OR$^x$ or —C(O)R$^x$. Thus when such a group is employed as a hydroxy protecting group, it may either be removed to generate the free hydroxy protecting group or it may remain as a part of the final product.

The reactive hydroxy groups in a compound of formula I' can be further reacted with a compound of the formula L—C(O)OR$^x$ (L being a leaving group) such as a chloroformate in the presence of a base such as tertiary amine to give the corresponding carbonate thereby providing further compounds within the scope of formula I. In addition, they may also react with a carboxylic acid R$^x$CO$_2$H, with an appropriate coupling agent known in the art, or with an acylating equivalent thereof (e.g. an anhydride, active ester or an acyl halide) to provide the corresponding ester.
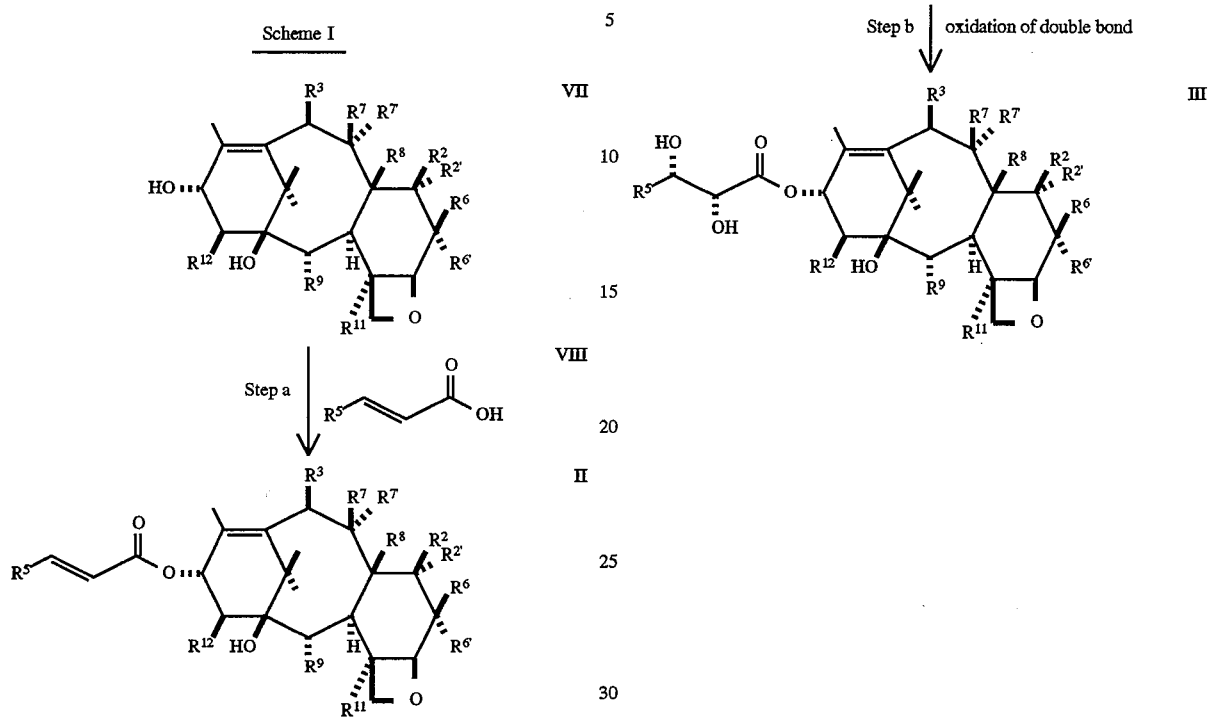
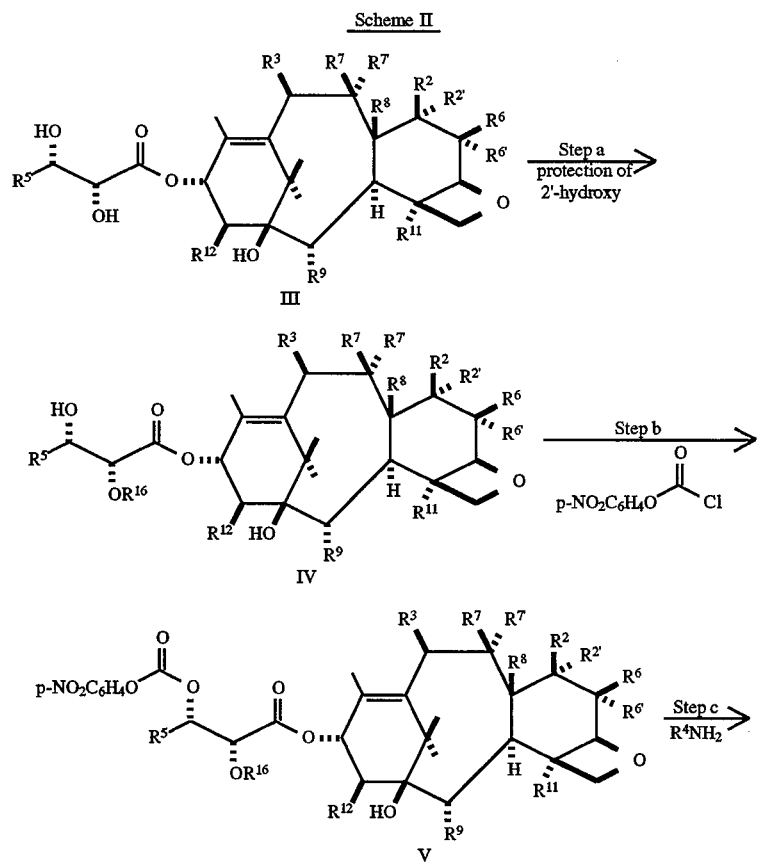

-continued
Scheme II

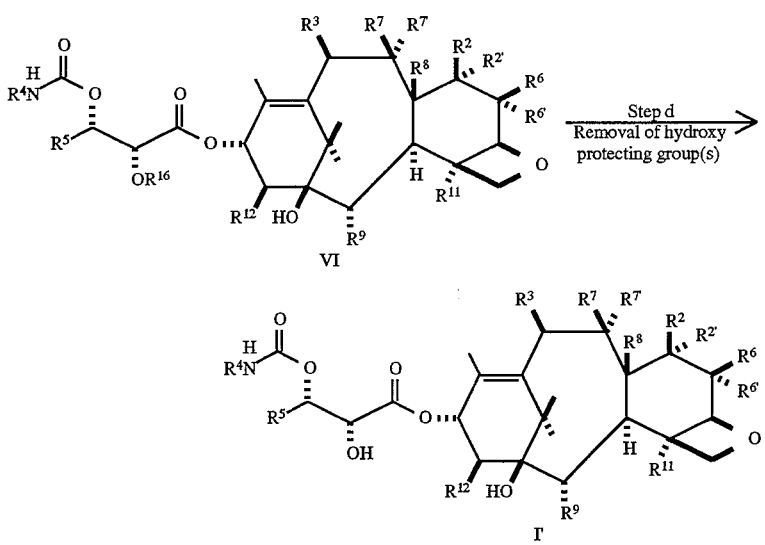

By now there are many publications teaching the introduction of a wide variety of groups onto a taxane core. By using these well established methods or obvious variants thereof, the starting taxanes of formula VII, or hydroxy protected analogues thereof, can be readily made. For example, for transforming C4-acetoxy into other functional groups see, S. H. Chen et al., *J. Organic Chemistry*, 59, pp 6156–6158 (1994) and PCT application WO 94/14787 published Jul. 7, 1994; for converting C2-benzoyloxy to other groups see, S. H. Chen et al, *Bioorganic and Medicinal Chemistry Letters*, Vol. 4, No. 3, pp 479–482 (1994); K. C. Nicolaou et al., *J. Am. Chem. Soc.*, 1995, 117, 2409 and European Patent Application 617,034A1 published Sep. 28, 1994; for modifying C10-acetyloxy see, K. V. Rao et al., *J. Med. Chem.*, 38, pp 3411–3414 (1995), J. Kant et al., *Tetrahedron Letters*, Vol. 35, No. 31, pp 5543–5546 (1994); and U.S. Pat. No. 5,294,637 issued Mar. 15, 1994; for making C10 and/or C7 unsubstituted (deoxy) derivatives see, European Patent Application 590,267A2 published Apr. 6, 1994 and PCT application WO 93/06093 published Apr. 1, 1993; for making 7β,8β-methano, 6α,7α-dihydroxy and 6,7-olefinic groups see, R. A. Johnson, *Tetrahedron Letters*, Vol. 35, No 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and G. I. Kingston, *Tetrahedron Letters*, Vol. 36, No. 17, pp 2901–2904 (1995); for making C7-epi-fluoro see, G. Roth et al, *Tetrahedron Letters*, Vol 36, pp 1609–1612 (1995); for forming C7 esters and carbonates see, U.S. Pat. No. 5,272,171 issued Dec. 21, 1993 and S. H. Chen et al., *Tetrahedron*, 49, No. 14, pp 2805–2828 (1993); for 9α- and 9β-hydroxy taxanes see, L. L. Klein, *Tetrahedron Letters*, Vol 34, No 13, pp 2047–2050 (1993), PCT application WO 94/08984 published Apr. 28, 1994, U.S. Pat. No. 5,352,806 issued Oct. 4, 1994, and PCT application WO 94/20485 published Sep. 15, 1994.

DESCRIPTION OF SPECIFIC EMBODIMENTS

The specific examples that follow illustrate the syntheses of the compounds of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); $(DHQ)_2PHAL$ (hydroquinine 1,4-phthalazinediyl diether).

Preparation 1. Compound IIa

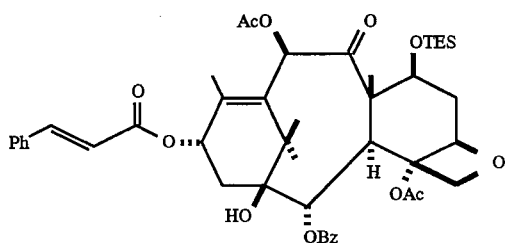

7-O-Triethylsilyl baccatin III (2.00 g, 2.86 mmol) was dissolved in toluene (20 mL). To this solution was added trans-cinnamic acid (0.91 g, 5.72 mmol) and DCC (1.20 g, 5.72 mmol) along with DMAP (0.50 g, 4.09 mmol). The reaction mixture was stirred at room temperature for 20 hr. The reaction mixture was then filtered and concentrated in vacuo. The residue was chromatographed (15–20% EtOAc/hexanes) to afford ~100% of the C-13 cinnamate ester IIa; $^1$H NMR (300 MHz, CDCl$_3$): δ8.08–8.06 (d, 2H), 7.84 (d, J=16.0 Hz, 1H), 7.62–7.43 (m, 7H), 6.53 (d, J=16.4 Hz, 1H), 6.50 (s, 1H), 6.16 (t, J=8.9 Hz, 1H), 5.69 (d, J=7.0 Hz, 1H), 4.97 (d, J=8.5 Hz, 1H), 4.50 (dd, J=6.7 Hz, J'=10.3 Hz, 1H), 4.24 (AB q, J=8.3 Hz, 2H), 3.88 (d, J=6.9 Hz, 1H), 2.60–0.55 (m, 37H, including singlets at 2.30, 2.19, 2.15, 1.71, 1.25, 1.21, 3H each).

HRMS calcd. for C$_{46}$H$_{58}$O$_{12}$SiNa (MNa$^+$): 853.3595, found: 853.3582.

Preparation 2. Compound IIb

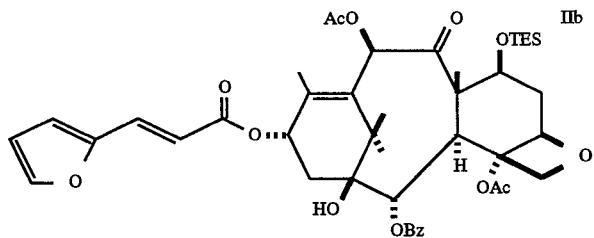

As in Preparation 1, compound IIb was prepared from 7-O-triethylsilyl baccatin III and furylacrylic acid; $^1$H NMR (300 MHz, CDCl$_3$): δ8.03–8.00 (m, 2H), 7.56–7.37 (m, 5H), 6.66 (m, 1H), 6.48 (m, 2H) 6.47 (s, 1H), 6.36 (d, J=15.7 Hz, 1H), 6.10 (t, J=8.3 Hz, 1H), 5.64 (d, J=7.0 Hz, 1H), 4.92 (d, J=8.2 Hz, 1H), 4.45 (dd, J=6.7 Hz, J'=10.2 Hz, 1H), 4.18 (AB q, J=8.2 Hz, 2H), 3.82 (d, J=6.9 Hz, 1H), 2.52–1.14 (m, 22H, including singlets at 2.28, 2.14, 2.08, 1.66, 1.19, 1.14, 3H each), 0.89 (m, 9H), 0.54 (m, 6H).

Preparation 3. Compound IIIa

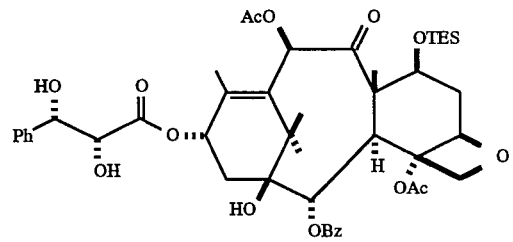

C-13-cinnamate ester IIa (1.10 g, 1.525 mmol) was suspended in a mixed solvent system consisting of t-BuOH (6.5 mL), H$_2$O (3.2 mL) and NMO (3.3 mL, 60% weight in H$_2$O). To this was added (DHQ)$_2$PHAL (Aldrich Chemical Company, 41.5 mg, 0.053 mmol) followed by K$_2$OsO$_4$ hydrate (9.7 mg, 0.0265 mmol). The resulting mixture was stirred at room temperature for 16 hr. Then the same amount of NMO, (DHQ)$_2$PHAL and K$_2$OsO$_4$ was further added, and the reaction was further stirred for 5 hr. At this point, the reaction was quenched with sodium bissulfite (5 g). After stirring at room temperature for 1 hr, the reaction mixture was filtered through Celite. The filtrates were diluted with EtOAc (100 mL), and washed with 5% HCl (2×10 mL). The organic layer was dried and concentrated in vacuo. The residue was purified by silica gel chromatography (eluted with 40–50% EtOAc/hexanes) to afford 909 mg (79%) of compound IIIa as a colorless powder; $^1$H NMR (300 MHz, CDCl$_3$): δ8.02–8.00 (d, 2H), 7.60–7.24 (m, 9H), 6.39 (s, 1H), 6.12 (t, 1H), 5.60 (d, J=7.1 Hz, 1H), 4.95 (t, J=4.5 Hz, 1H), 4.85 (d, J=8.6 Hz, 1H), 4.39 (dd, J=6.7 Hz, J'=10.4 Hz, 1H), 4.31 (dd, J=4.4 Hz, J'=8.0 Hz, 1H), 4.14 (AB q, J=8.4 Hz, 2H), 3.71 (d, J=7.0 Hz, 1H), 3.52 (OH), 2.46 (m, 1H), 2.25–0.49 (m, 36H, including singlets at 2.15, 2.12, 2.03, 1.63, 1.16, 1.13, 3H each); $^{13}$C NMR (75 MHz, CDCl$_3$): δ201.8, 172.3, 170.1, 169.1, 166.7, 139.9, 139.3, 133.7, 133.6, 130.0, 129.2, 128.6, 128.5, 128.4, 128.3, 128.26, 126.5, 126.3, 84.0, 80.9, 78.6, 76.3, 75.7, 74.9, 74.7, 72.1, 71.4, 58.3, 46.6, 43.1, 37.0, 35.1, 26.4, 22.2, 20.9, 20.7, 14.2, 9.9, 6.6, 5.1.

HRMS calcd. for C$_{54}$H$_{65}$NO$_{14}$SiNa (MNa$^+$): 1002.4072, found: 1002.4080.

Preparation 4. Compound IIIb

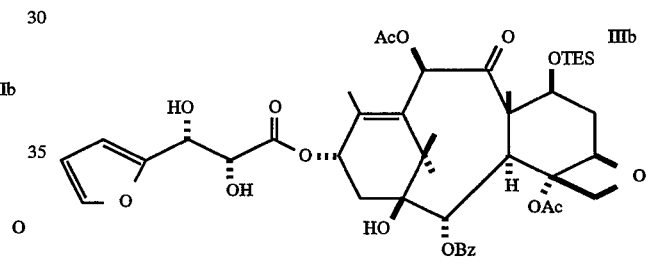

As in Preparation 3, compound IIIb was prepared from compound IIb; $^1$H NMR (300 MHz, CDCl$_3$): δ8.04–8.01 (m, 2H), 7.60–7.37 (m, 4H), 6.40–6.33 (m, 3H), 6.17 (t, J=8.8 Hz, 1H), 5.62 (d, J=7.0 Hz, 1H), 5.02 (bs, 1H), 4.88 (d, J=9.2 Hz, 1H), 4.55 (bs, 1H), 4.41 (dd, J=6.7 Hz, J'=10.1 Hz, 1H), 4.17 (AB q, J=8.3 Hz, 2H), 3.76 (d, J=6.9 Hz, 1H), 3.67 (m, 2H (OH)), 2.50–1.13 (m, 22H, including singlets at 2.27, 2.12, 2.00, 1.64, 1.17, 1.13, 3H each), 0.88 (m, 9H), 0.52 (m, 6H).

Preparation 5. Compound IVa

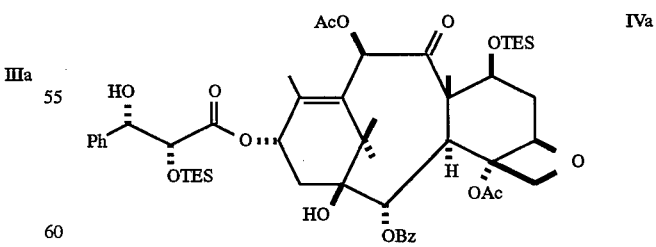

Compound IIIa (727 mg, 0.841 mmol) was dissolved in dry THF (16.8 mL). To this solution at 0° C. was added imidazole (68.6 mg, 1.009 mmol), followed by TESCl (141.2 μL, 0.841 mmol). After stirring at 0° C. for 1 hr, the reaction mixture was diluted with EtOAc (120 mL), and washed with water (2×10 mL) and brine (10 mL). The organic layer was dried and concentrated in vacuo. The resulting residue was purified by silica gel chromatography (20–30–50% EtOAc/hexanes) to provide 249 mg (30%) of compound IVa along with 150 mg of the recovered starting material; $^1$H NMR (300 MHz, CDCl$_3$): δ8.07–8.04 (m, 2H), 7.64–7.26 (m, 9H), 6.45 (s, 1H), 6.07 (t, 1H), 5.64 (d, J=7.1 Hz, 1H), 5.09 (d, J=3.6 Hz, 1H), 4.90 (d, J=8.2 Hz, 1H), 4.46 (dd, J=6.6 Hz, J'=10.4 Hz, 1H), 4.19 (dd, J=3.6 Hz, J'=8.7 Hz, 1H), 4.20 (AB q, J=8.3 Hz, 2H), 3.78 (d, J=7.0 Hz, 1H), 3.12 (OH), 2.60–0.45 (m, 52H, including singlets at 2.24, 2.18, 2.06, 1.67, 1.25, 1.21, 3H each).

HRMS calcd. for C$_{52}$H$_{74}$O$_{14}$Si$_2$Na (MNa$^+$): 1001.4515, found: 1001.4479.

Preparation 6. Compound IVb

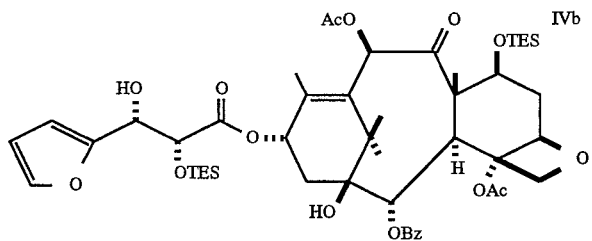

As in Preparation 5, compound IVb was prepared from compound IIIb; $^1$H NMR (300 MHz, CDCl$_3$): δ8.05–8.02 (m, 2H), 7.60–7.36 (m, 4H), 6.42 (s, 1H), 6.33 (m, 2H), 6.19 (t, J=9.3 Hz, 1H), 4.94 (dd, J=4.3 Hz, J'=7.7 Hz, 1H), 4.90 (d, J=8.2 Hz, 1H), 4.61 (d, J=4.3 Hz, 1H), 4.44 (dd, J=6.6 Hz, J'=10.4 Hz, 1H), 4.19 (AB q, J=8.3 Hz, 2H), 3.79 (d, J=7.0 Hz, 1H), 3.08 (d, J=7.7 Hz, 1H), 2.50–0.50 (m, 52H, including singlets at 2.34, 2.12, 1.94, 1.65, 1.17, 1.15, 3H each).

Preparation 7. Compound Va

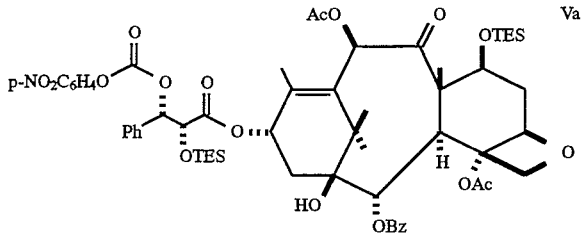

Compound IVa (387.7 mg (0.396 mmol) was dissolved in CH$_2$Cl$_2$ (8 mL). This solution was treated at 0° C. with triethylamine (60.8 µL, 0.436 mmol) followed by p-nitrophenylchloroformate (87.9 mg, 0.436 mmol). After stirring 1 hr at 0° C., the reaction was stirred at room temperature overnight. The solvent was then removed, and the residue was chromatographed (20–30% EtOAc/hexanes) to provide 458 mg (100%) of the desired product Va; $^1$H NMR (300 MHz, CDCl$_3$): δ8.28–8.23 (m, 2H), 8.04–8.00 (m, 2H), 7.68–7.31 (m, 10H), 7.12 (m, 1H), 6.37 (s, 1H), 5.90 (t, J=8.3 Hz, 1H), 5.56 (d, J=7.1 Hz, 1H), 5.04 (AB q, J=7.4 Hz, 2H), 4.87 (d, J=8.0 Hz, 1H), 4.38 (dd, J=6.5 Hz, J'=10.4 Hz, 1H), 4.15 (AB q, J=8.6 Hz, 2H), 3.65 (d, J=7.1 Hz, 1H), 2.60–0.45 (m, 52H, including singlets at 2.22, 2.03, 1.92, 1.61, 1.26, 1.08, 3H each).

Preparation 8. Compound Vb

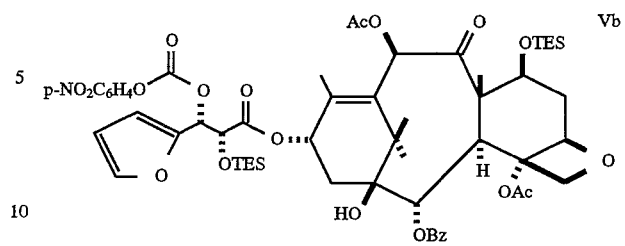

As in Preparation 7, compound IVb afforded compound Vb; $^1$H NMR (300 MHz, CDCl$_3$): δ8.22–8.19 (m, 2H), 8.07–8.03 (m, 2H), 7.60–7.31 (m, 6H), 6.58 (d, J=3.2 Hz, 1H), 6.38 (bs, 2H), 6.15 (m, 2H), 5.62 (d, J=7.1 Hz, 1H), 4.91 (d, J=8.5 Hz, 2H), 4.44 (dd, d=6.6 Hz, J'=10.3 Hz, 1H), 4.20 (AB q, J=8.3 Hz, 2H), 3.80 (d, J=7.1 Hz, 1H), 2.51–0.50 (m, 52H, including singlets at 2.49, 2.15, 1.76, 1.66, 1.18, 1.13, 3H each).

Preparation 9. Compound VIa

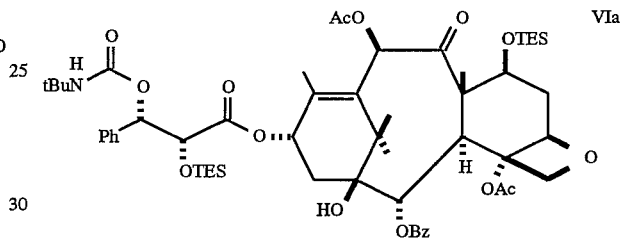

Compound Va (211 mg, 0.185 mmol) was dissolved in dry THF (4 mL). This solution was treated at room temperature with t-butylamine (116.4 µL, 1.108 mmol) for 15 hr. The solvent was then removed, and the residue was purified by silica gel chromatography (20–25% EtOAc/hexanes) to afford 194 mg (97%) of desired product VIa; $^1$H NMR (300 MHz, CDCl$_3$): δ8.05–8.02 (m, 2H), 7.68–7.26 (m, 8H), 7.10 (m, 1H), 6.39 (s, 1H), 5.89–5.82 (m, 2H), 5.56 (d, J=7.1 Hz, 1H), 5.04–4.87 (m, 3H), 4.77 (s, 1H), 4.43 (dd, J=6.6 Hz, J'=10.4 Hz, 1H), 4.15 (AB q, J=8.0 Hz, 2H), 3.67 (d, J=7.1 Hz, 1H), 2.60–0.45 (m, 61H, including singlets at 2.26, 2.14, 1.92, 1.69, 1.14, 1.09, 3H each, 1.24, 9H).

HRMS calcd. for C$_{57}$H$_{83}$NO$_{15}$Si$_2$Na (MNa$^+$): 1100.5199, found: 1100.5172.

Preparation 10. Compound VIb

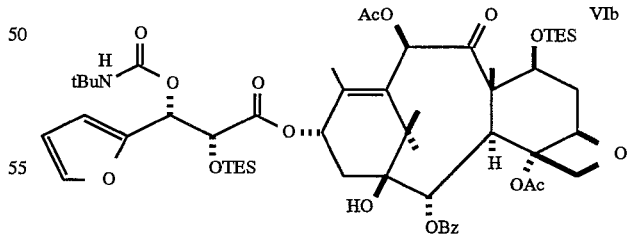

As in Preparation 9, compound Vb afforded compound VIb; $^1$H NMR (300 MHz, CDCl$_3$): δ8.11–8.08 (m, 2H), 7.59–7.43 (m, 3H), 7.38 (s, 1H), 6.43 (s, 1H), 6.34 (bs, 2H), 6.12 (t, 1H), 6.06 (d, J=5.1 Hz, 1H), 5.65 (d, J=7.1 Hz, 1H), 5.31 (bs, 1H), 4.93 (d, J=8.3 Hz, 1H), 4.72 (d, J=5.1 Hz, 1H), 4.44 (dd, J=6.7 Hz, J'=10.3 Hz, 1H), 4.22 (AB q, J=8.3 Hz, 2H), 3.84 (d, J=7.1 Hz, 1H), 2.56–0.49 (m, 61H, including singlets at 2.56, 2.16, 1.89, 1.70, 1.20, 1.16, 3H each, 1.26, 9H).

Preparation 11. Compound Ia

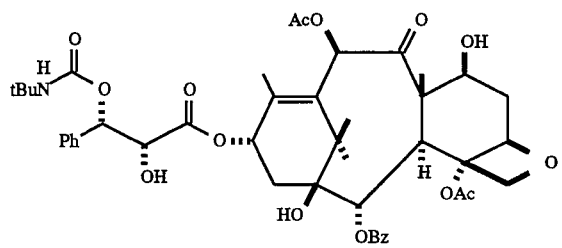

Compound VIa was dissolved in acetonitrile (3.5 mL). The resulting solution was treated at 0° C. with 6N HCl (0.12 mL, 0.721 mmol). After 3 hr at 0° C., the reaction mixture was diluted with EtOAc (60 mL), and washed with brine (2×6 mL). The organic layer was dried and concentrated. The residue was chromatographed on silica gel (eluted with 50–60% EtOAc/hexanes) to afford 110.2 mg (72%) of the desired product as a colorless solid; $^1$H NMR (300 MHz, CDCl$_3$): δ8.04–8.01 (m, 2H), 7.69–7.50 (m, 3H), 7.36–7.34 (m, 5H), 7.16 (m, 1H), 6.24 (s, 1H), 6.01 (t, J=8.1 Hz, 1H), 5.57 (d, J=7.1 Hz, 1H), 5.02 (m, 3H), 4.90 (d, J=7.9 Hz, 1H), 4.40 (m, 1H), 4.16 (AB q, J=8.3 Hz, 2H), 3.68 (d, J=7.0 Hz, 1H), 3.18 (OH), 2.57–1.60 (m, 16H, including singlets at 2.23, 2.19, 1.89, 1.60, 3H each), 1.28 (s, 9H), 1.18 (s, 3H), 1.07 (s, 3H); $^{13}$C NMR (75 MHz, CDCl$_3$): δ203.7, 171.2, 170.0, 166.8, 152.8, 143.3, 138.0, 133.7, 132.2, 130.0, 129.1, 128.7, 128.5, 126.6, 84.3, 80.6, 79.0, 76.1, 75.5, 75.0, 73.6, 71.8, 71.0, 58.2, 50.7, 45.4, 42.9, 35.3, 34.8, 28.6, 26.6, 22.2, 21.9, 20.7, 14.6, 9.5.

HRMS calcd. for C$_{45}$H$_{55}$NO$_{15}$Na (MNa$^+$): 872.3469, found: 872.3456.

Preparation 13. Compound Ic

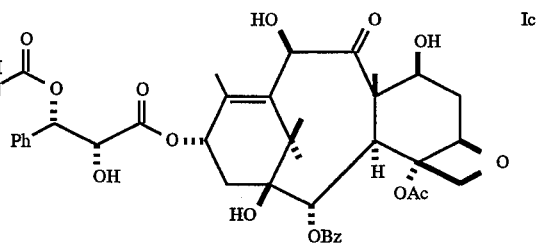

Compound Ia (34.6 mg, 0.041 mmol) was dissolved in H$_2$O(0.75 mL) and 30% H$_2$O$_2$ (0.75 mL). To this solution was added sodium bicarbonate (75 mg). The resulting suspension was stirred vigorously for 15 hr. The reaction mixture diluted with EtOAc (50 mL), and washed with brine (3×5 mL). The organic layer was dried and concentrated. The residue was chromographed on silica gel (eluted with 50–70% EtOAc/hexanes) to afford 13.8 mg (42%) of the desired product; $^1$H NMR (300 MHz, CDCl$_3$): δ8.05–8.02 (m, 2H), 7.69–7.51 (m, 3H), 7.38–7.36 (m, 5H), 7.20 (m, 1H), 6.04 (t, J=8.7 Hz, 1H), 5.60 (d, J=7.1 Hz, 1H), 5.17 (s, 1H), 5.08 (m, 2H), 4.98 (s, 1H), 4.90 (d, J=8.1 Hz, 1H), 4.26 (d, J=8.4 Hz, 1H), 4.19 (m, 1H), 4.11 (d, J=8.4 Hz, 1H), 3.82 (d, J=7.1 Hz, 1H), 3.07 (OH), 2.60–1.69 (m, 13H, including singlets at 2.23, 1.89, 1.69, 3H each), 1.29 (s, 9H), 1.18 (s, 3H), 1.06 (s, 3H); $^{13}$C NMR (75 MHz, CDCl$_3$): δ211.5, 169.7, 166.8, 152.8, 139.3, 135.2, 133.7, 130.0, 129.2, 128.6, 128.5, 126.5, 84.1, 80.6, 78.8, 76.5, 76.3, 74.8, 74.3, 73.7, 71.6, 71.3, 57.3, 50.8, 46.2, 42.8, 36.6, 35.0, 28.5, 26.3, 22.2, 20.7, 14.1, 9.8.

HRMS calcd. for C$_{43}$H$_{53}$NO$_{14}$Na (MNa$^+$): 830.3364, found: 830.3375.

Preparation 12. Compound Ib

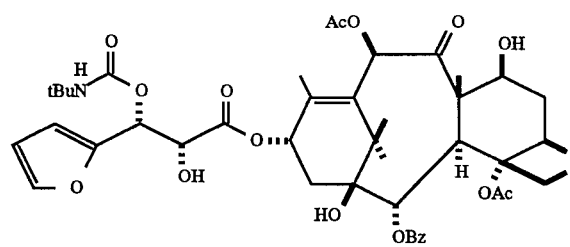

As in Preparation 11, compound VIb afforded compound Ib; $^1$H NMR(300 MHz, CDCl$_3$): δ8.10–8.04 (m, 2H), 7.62–7.42 (m, 4H), 6.45 (d, J=3.1 Hz, 1H), 6.38 (m, 1H), 6.29 (s, 1H), 6.20 (t, J=9.1 Hz, 1H), 6.11 (d, J=2.7 Hz, 1H), 5.65 (d, J=7.0 Hz, 1H), 5.09 (bs, 1H), 4.94 (d, J=8.9 Hz, 1H), 4.64 (dd, J=3.0 Hz, J'=8.1 Hz, 1H), 4.41 (m, 1H), 4.21 (AB q, J=8.3 Hz, 2H), 3.79 (d, J=6.8 Hz, 1H), 3.42 (d, J=8.3 Hz, 1H), 2.61–1.13 (m, 3H, including singlets at 2.39, 2.24, 1.87, 1.66, 1.24, 1.13, 3H each, 1.21, 9H).

Preparation 14. Compound Id

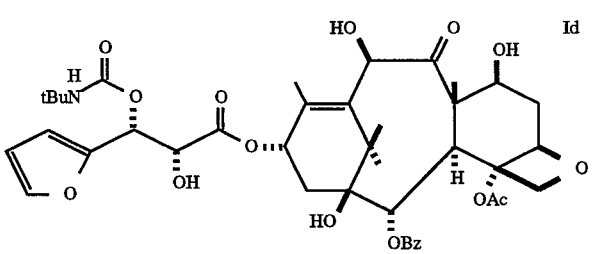

As in Preparation 13, compound Ib was converted to compound Id; $^1$H NMR (300 MHz, CDCl$_3$): δ8.12–8.08 (m, 2H), 7.64–7.43 (m, 4H), 6.46–6.37 (m, 2H), 6.21 (t, J=8.9 Hz, 1H), 6.11 (d, J=2.7 Hz, 1H), 5.67 (d, J=7.1 Hz, 1H), 5.21 (s, 1H), 5.04 (s, 1H), 4.93 (d, J=8.1 Hz, 1H), 4.64 (dd, J=3.1 Hz, J'=8.1 Hz, 1H), 4.24 (s, 1H), 4.25 (AB q, J=8.4 Hz, 2H), 3.91 (d, J=7.0 Hz, 1H), 3.36 (d, J=8.3 Hz, 1H), 2.60–1.08 (m, 28H, including singlets at 2.40, 1.91, 1.75, 1.23, 1.12, 3H each, 1.22, 9H).

Preparation 15.

Following the procedures outlined in Preparations 1–12, the following compound were prepared:

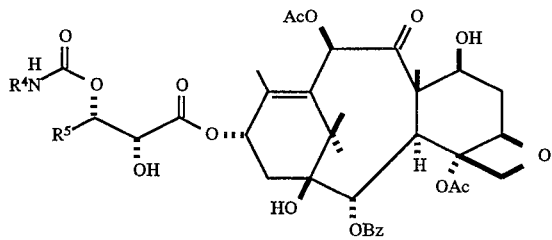

Ie: R⁴ = isopropyl;  R⁵ = Ph

If: R⁴ = isopropyl;  R⁵ = 2-furyl

Ig: R⁴ = cyclobutyl;  R⁵ = 2-furyl

¹H NMR of compound Ie (300 MHz, CDCl₃): δ8.11–8.08 (m, 2H), 7.65–7.31 (m, 8H), 6.28–6.19 (m, 3H), 6.05 (d, J=3.0 Hz, 1H), 5.65 (d, J=7.1 Hz, 1H), 5.07 (d, J=7.9 Hz, 1H), 4.95 (d, J=8.5 Hz, 1H), 4.51 (bs, 1H), 4.40 (dd, J=6.8 Hz, J'=10.1 Hz, 1H), 4.22 (AB q, J=8.4 Hz, 2H), 3.77 (d, J=7.0 Hz, 1H), 3.67 (m, 1H), 3.07 (m, 1H), 2.59–1.03 (m, 28H, including singlets at 2.43, 2.25, 1.87, 1.67, 1.26, 1.14, 3H each).

HRMS calcd. for C₄₄H₅₄NO₁₅ (MH⁺): 836.3494; found: 836.3501.

¹H NMR of compound If (300 MHz, CDCl₃): δ8.12–8.06 (m, 2H), 7.64–7.43 (m, 4H), 6.48–6.38 (m, 2H), 6.28 (s, 1H), 6.23 (t, J=8.6 Hz, 1H), 6.12 (d, J=2.9 Hz, 1H), 5.66 (d, J=7.0 Hz, 1H), 4.94 (m, 2H), 4.67 (dd, J=3.1 Hz, J'=7.8 Hz, 1H), 4.40 (m, 1H), 4.23 (AB q, J=8.4 Hz, 2H), 3.79 (d, J=6.9 Hz, 1H), 3.70 (m, 1H), 3.30 (d, J=8.0 Hz, 1H), 2.56–1.13 (m, 22H, including singlets at 2.41, 2.24, 1.87, 1.68, 1.25, 1.14, 3H each), 1.09 (d, J=6.5 Hz, 3H), 1.04 (d, J=6.4 Hz, 3H).

¹H NMR of compound Ig (300 MHz, CDCl₃): δ8.13–8.10 (m, 2H), 7.62–7.42 (m, 4H), 6.46 (d, J=3.1 Hz, 1H), 6.38 (bs, 1H), 6.28 (s, 1H), 6.23 (t, J=8.7 Hz, 1H), 6.12 (d, J=3.0 Hz, 1H), 5.65 (d, J=7.1 Hz, 1H), 5.35 (d, J=8.2 Hz, 1H), 4.94 (d, J=8.6 Hz, 1H), 4.66 (dd, J=3.2 Hz, J'=7.9 Hz, 1H), 4.42 (m, 1H), 4.24 (AB q, J=8.4 Hz, 2H), 4.00 (m, 1H), 3.79 (d, J=7.0 Hz, 1H), 3.39 (d, J=7.9 Hz, 1H), 2.61–1.13 (m, 28H, including singlets at 2.41, 2.23, 1.86, 1.67, 1.25, 1.14, 3H each); ¹³C NMR (75 MHz, CDCl₃): δ203.6, 171.5, 171.1, 170.6, 166.9, 153.6, 149.3, 142.7, 142.1, 133.6, 132.9, 130.1, 129.0, 128.6, 110.6, 109.4, 84.3, 80.9, 79.1, 76.3, 75.4, 74.9, 72.3, 72.0, 71.9, 69.6, 58.4, 46.2, 45.6, 43.1, 35.5, 35.3, 30.9, 26.6, 22.3, 21.8, 20.7, 14.7, 14.6, 9.5.

Preparation 16. Compound IIc

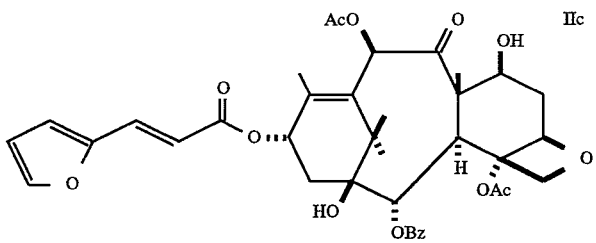

Compound IIb (2.10 g, 2.560 mmol) was dissolved in CH₃CN (30 mL). To this solution at 0° C. was added 6N HCl (1.28 mL, 7.683 mmol). After stirring at 0° C. for 3 hr, the reaction was diluted with EtOAc (150 mL), and the resulting mixture was washed with brine (2×20 mL). The organic layer was dried and concentrated in vacuo. The residue was purified by silica gel chromatography (40–60% EtOAc/ hexanes) to afford 1.48 g (82%) of compound IIc; ¹H NMR (300 MHz, CDCl₃): δ8.07–8.04 (m, 2H), 7.59–7.43 (m, 5H), 6.71 (d, J=3.4 Hz, 1H), 6.52 (m, 1H), 6.38 (d, J=16.8 Hz, 1H), 6.33 (s, 1H), 6.19 (t, 1H), 5.67 (d, J=7.0 Hz, 1H), 4.98 (d, J=7.8 Hz, 1H), 4.46 (m, 1H), 4.23 (AB q, J=8.4 Hz, 2H), 3.85 (d, J=7.0 Hz, 1H), 2.60–1.14 (m, 22H, including singlets at 2.32, 2.25, 1.98, 1.69, 1.25, 1.15, 3H each).

Preparation 17. Compound IId

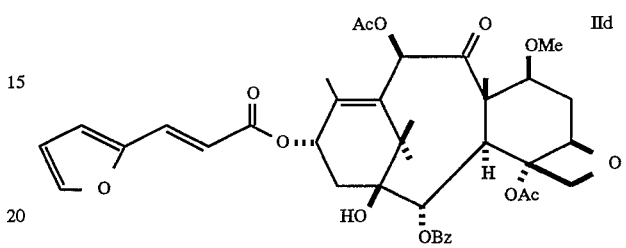

Compound IIc (1.37 g, 1.94 mmol) was dissolved in dry THF (30 mL). This solution was treated at –78° C. with LiHMDS (2.33 mL, 1M, 2.33 mmol) for 30 mins, then followed by MeOTf (328.3 uL, 2.91 mmol). The reaction was stirred at –40° C. for 5 hr. At this point, the reaction was quenched with NH₄Cl saturated solution (10 mL), and extracted with EtOAc (2×75 mL). The organic layer was washed with brine, then dried and concentrated. The resulting residue was chromatographed on silica gel (35–50% EtOAc/hexanes) to provide 717 mg (52%) of the desired compound; ¹H NMR (300 MHz, CDCl₃): δ8.04–8.01 (m, 2H), 7.58–7.39 (m, 4H), 6.69 (d, J=3.4 Hz, 1H), 6.50 (m, 1H), 6.44 (s, 1H), 6.37 (d, J=15.7 Hz, 1H), 6.14 (t, J=8.3 Hz, 1H), 5.63 (d, J=6.9 Hz, 1H), 5.98 (d, J=8.7 Hz, 1H), 4.20 (AB q, J=8.4 Hz, 2H), 3.90 (m, 2H), 3.35 (s, 3H), 2.73 (m, 1H), 2.50–1.17 (m, 21H, including singlets at 2.29, 2.20, 2.04, 1.71, 3H each, 1.18, 6H).

Preparation 18. Compound IIIc

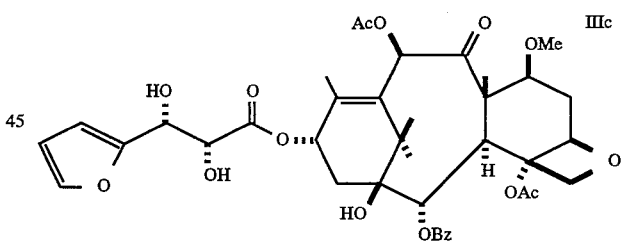

Compound IId (231 mg, 0.321 mmol) was suspended in a mixed solvent system consisting of t-BuOH (2 mL), H₂O (1 mL), NMO (1 mL, 60% wt in H₂O) and THF (0.5 mL). To this suspension was added (DHQ)₂PHAL (20 mg, 0.026 mmol), followed by K₂OsO₄ hydrate (4.7 mg, 0.013 mmol). The reaction mixture was stirred at room temperature for 16 hr, and then quenched with sodium bissulfite (0.70 g). The reaction mixture was then filtered. After usual extraction (EtOAc) and silica gel chromatography (50–70% EtOAc/ hexanes), 56 mg (23%) of compound IIIc was obtained; ¹H NMR (300 MHz, CDCl₃): δ8.07–8.04 (m, 2H), 7.61–7.41 (m, 4H), 6.44–6.37 (m, 3H), 6.22 (t, J=8.9 Hz, 1H), 5.64 (d, J=6.9 Hz, 1H), 5.08 (d, J=2.6 Hz, 1H), 4.95 (d, J=8.8 Hz, 1H), 4.60 (d, J=2.8 Hz, 1H), 4.21 (AB q, J=8.4 Hz, 2H), 3.86 (m, 2H), 3.33 (s, 3H), 2.72 (m, 1H), 2.32–1.06 (m, 21H, including singlets at 2.32, 2.21, 1.97, 1.71, 1.21, 1.19, 3H each).

Preparation 19

Following essentially the procedures described in Preparations 5–12, compounds Ih and Ii can be obtained from compound IIIc.

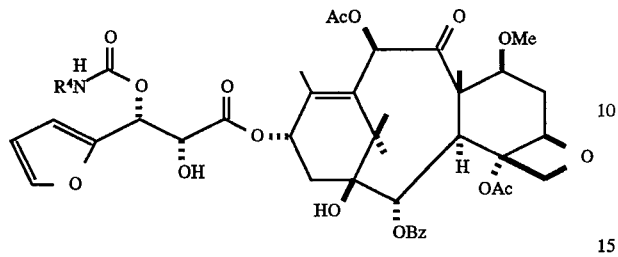

Ih:  R⁴ = t-Bu

Ii:  R⁴ = cyclobutyl $^1$H NMR of compound Ih (300 MHz, CDCl$_3$): δ8.10–8.07 (m, 2H), 7.62–7.43 (m, 4H), 6.46–6.37 (m, 3H), 6.18 (t, J=8.5 Hz, 1H), 6.11 (d, J=2.8 Hz, 1H), 5.64 (d, J=7.0 Hz, 1H), 5.16 (s, 1H), 4.96 (d, J=8.4 Hz, 1H), 4.66 (d, J=2.8 Hz, 1H), 4.21 (AB q, J=8.5 Hz, 2H), 3.91–3.83 (m, 2H), 3.33 (s, 3H), 2.60–1.19 (m, 31H, incl. singlets at 2.41, 2.21, 1.95, 1.71, 1.21, 1.19, 3H, 1.24, 9H). $^{13}$C NMR (75 MHz, CDCl$_3$): δ202.1, 171.7, 170.5, 169.3, 166.8, 153.0, 149.5, 142.6, 140.1, 133.5, 133.4, 130.0, 129.1, 128.5, 110.6, 109.2, 84.0, 81.4, 80.3, 78.6, 76.3, 74.6, 74.5, 72.2, 72.0, 69.1, 57.4, 57.0, 50.6, 47.1, 43.2, 35.1, 32.1, 28.5, 26.4, 22.4, 21.1, 20.8, 14.5, 10.2.

$^1$H NMR of compound Ii (300 MHz, CDCl$_3$): δ8.10–8.07 (m, 2H), 7.60–7.42 (m, 4H), 6.47–6.37 (m, 3H), 6.15 (t, J=8.7 Hz, 1H), 6.10 (d, J=3.1Hz, 1H), 5.64 (d, J=7.0 Hz, 1H), 5.44 (d, J=8.2 Hz, 1H), 4.96 (d, J=9.3 Hz, 1H), 4.66 (d, J=2.7 Hz, 1H), 4.21 (AB q, J=8.4 Hz, 2H), 4.03 (m, 1H), 3.91–3.81 (m, 2H), 3.33 (s, 3H), 2.70 (m, 1H), 2.42–1.18 (m, 27H, incl. singlets at 2.42, 2.21, 1.93, 1.71, 1.21, 1.18, 3H each). $^{13}$C NMR (75 MHz, CDCl$_3$): δ202.1, 171.4, 170.7, 169.3, 166.8, 153.7, 149.3, 142.7, 140.0, 133.6, 133.5, 130.0, 129.1, 128.5, 126.0, 115.4, 110.6, 109.5, 84.0, 81.4, 80.3, 78.7, 76.3, 74.5, 72.3 72.0, 69.6, 57.4, 57.0, 47.1, 46.2, 43.2, 35.1, 32.1, 31.0, 30.9, 26.5, 22.4, 21.2, 20.8, 14.6, 14.4, 10.3.

Following substantially the procedures described above, the following compounds within the scope of this invention, can be synthesized.

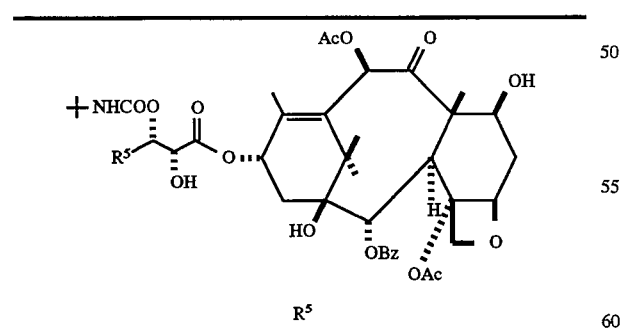

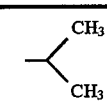

3-furyl
p-fluorophenyl p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

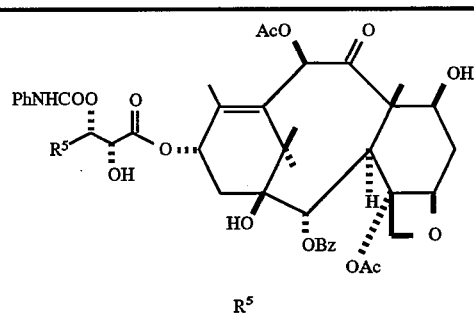

R⁵

$\underset{CH_3}{\overset{CH_3}{\diagup}}$ 3-furyl
2-furyl
p-fluorophenyl
p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

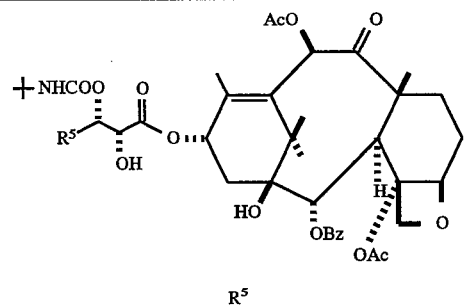

3-furyl
2-furyl
p-fluorophenyl

| 19 -continued | 20 -continued |
|---|---|
| p-chlorophenyl<br>p-methylphenyl<br>p-methoxyphenyl<br>p-bromophenyl<br>p-hydroxyphenyl<br>p-aminophenyl<br>p-nitrophenyl<br>2-thienyl<br>3-thienyl<br>cyclohexyl<br>cyclopentyl<br>cyclobutyl<br>cyclopropyl<br>isobutenyl<br>isopropyl<br>isobutyl | p-chlorophenyl<br>p-methylphenyl<br>p-methoxyphenyl<br>p-bromophenyl<br>p-hydroxyphenyl<br>p-aminophenyl<br>p-nitrophenyl<br>2-thienyl<br>3-thienyl<br>cyclohexyl<br>cyclopentyl<br>cyclobutyl<br>cyclopropyl<br>isobutenyl<br>isopropyl<br>isobutyl |
| 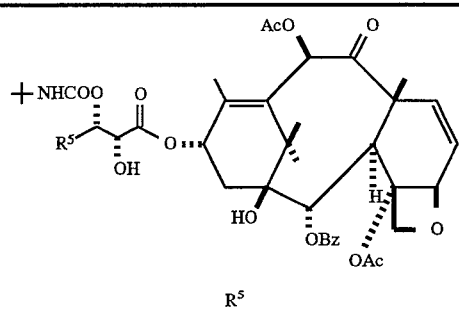 | 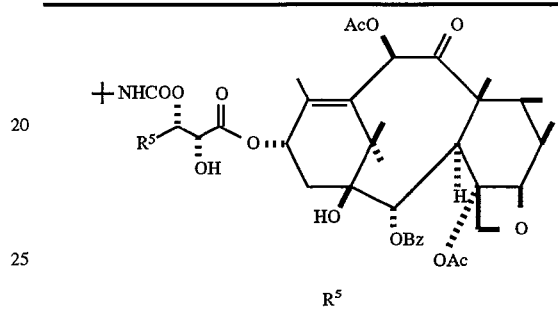 |
| $R^5$ | $R^5$ |
|  |  |
| 3-furyl<br>2-furyl<br>p-fluorophenyl<br>p-chlorophenyl<br>p-methylphenyl<br>p-methoxyphenyl<br>p-bromophenyl<br>p-hydroxyphenyl<br>p-aminophenyl<br>p-nitrophenyl<br>2-thienyl<br>3-thienyl<br>cyclohexyl<br>cyclopentyl<br>cyclobutyl<br>cyclopropyl<br>isobutenyl<br>isopropyl<br>isobutyl | 3-furyl<br>2-furyl<br>p-fluorophenyl<br>p-chlorophenyl<br>p-methylphenyl<br>p-methoxyphenyl<br>p-bromophenyl<br>p-hydroxyphenyl<br>p-aminophenyl<br>p-nitrophenyl<br>2-thienyl<br>3-thienyl<br>cyclohexyl<br>cyclopentyl<br>cyclobutyl<br>cyclopropyl<br>isobutenyl<br>isopropyl<br>isobutyl |
| 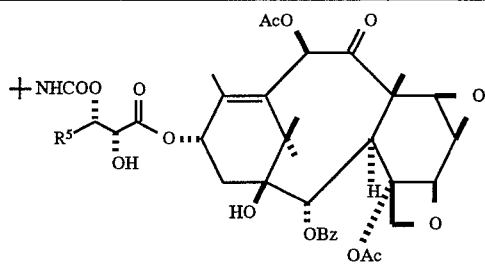 | 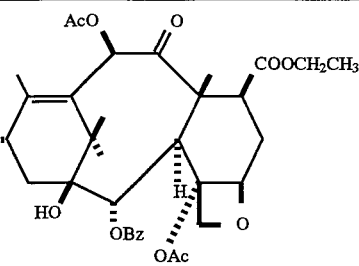 |
| $R^5$ | $R^5$ |
|  |  |
| 3-furyl<br>2-furyl<br>p-fluorophenyl | 3-furyl<br>2-furyl<br>p-fluorophenyl |

21

-continued p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

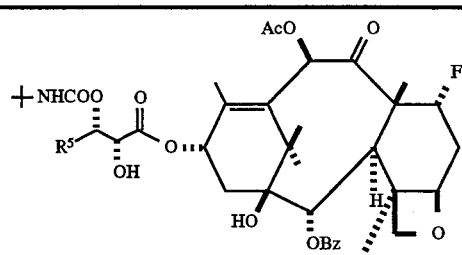

R⁵

3-furyl
2-furyl
p-fluorophenyl
p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

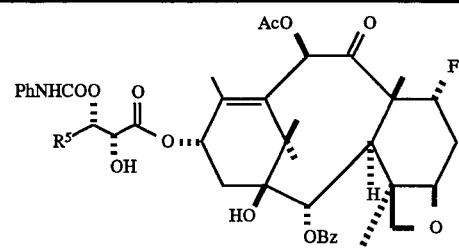

R⁵

3-furyl
2-furyl
p-fluorophenyl

22

-continued p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

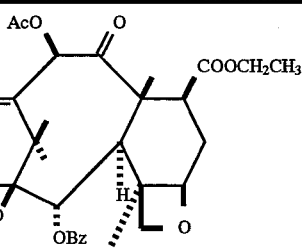

R⁵

3-furyl
2-furyl
p-fluorophenyl
p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

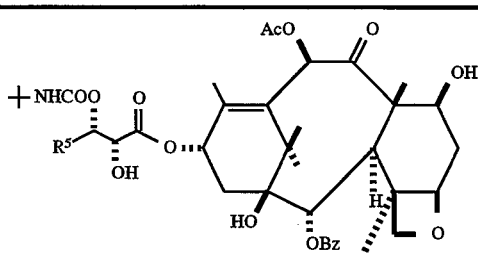

R⁵

3-furyl
p-fluorophenyl
p-chlorophenyl

23
-continued p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

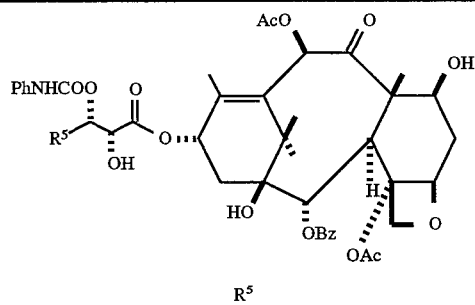

$R^5$

3-furyl
2-furyl
p-fluorophenyl
p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

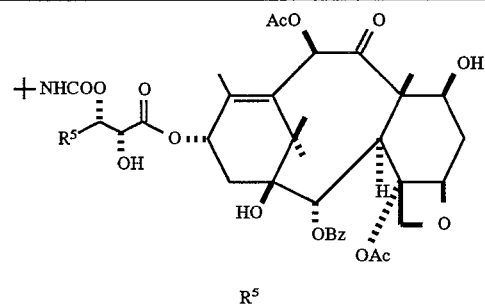

$R^5$

3-furyl
p-fluorophenyl
p-chlorophenyl
p-methylphenyl

24
-continued p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

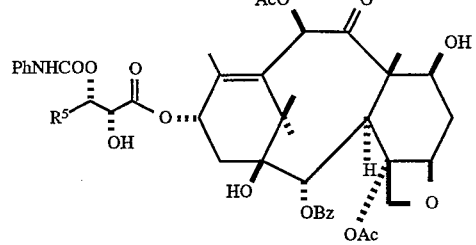

$R^5$

3-furyl
2-furyl
p-fluorophenyl
p-chlorophenyl
p-methylphenyl
p-methoxyphenyl
p-bromophenyl
p-hydroxyphenyl
p-aminophenyl
p-nitrophenyl
2-thienyl
3-thienyl
cyclohexyl
cyclopentyl
cyclobutyl
cyclopropyl
isobutenyl
isopropyl
isobutyl

$R^j$ cyclopropyl
cyclobutyl
n-propyl
OMe
OEt

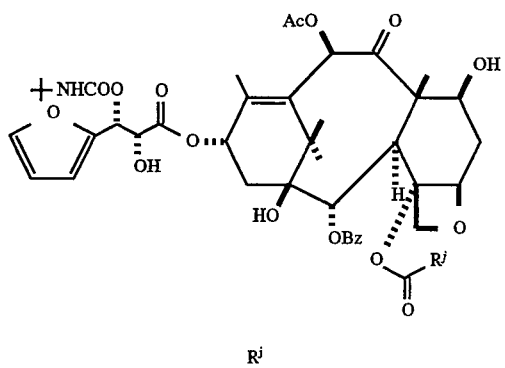

| $R^j$ |
| --- |
| cyclopropyl |
| cyclobutyl |
| n-propyl |
| OMe |
| OEt |

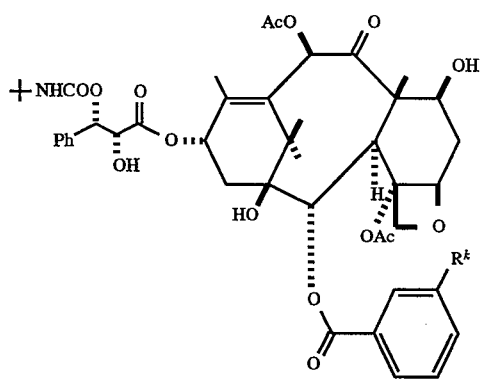

| $R^k$ |
| --- |
| $N_3$ |
| OMe |
| Cl |
| CN |

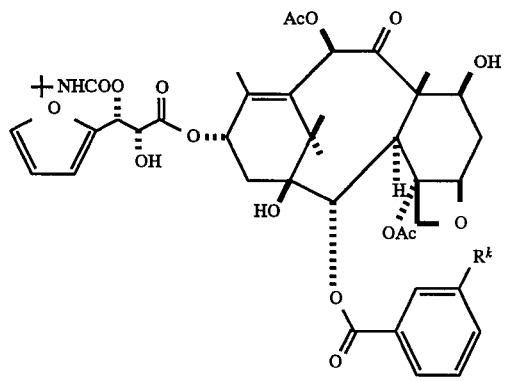

| $R^k$ |
| --- |
| $N_3$ |
| OMe |
| Cl |
| CN |

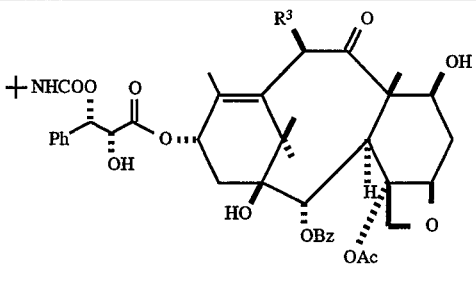

| $R^3$ |
| --- |
| MeO |
| $-OCO_2Me$ |
| $-OC(O)NMe_2$ |
| $-OC(O)nBu$ |

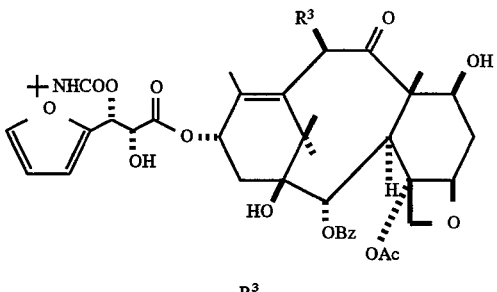

| $R^3$ |
| --- |
| MeO |
| $-OCO_2Me$ |
| $-OC(O)NMe_2$ |
| $-OC(O)nBu$ |

The compounds of this invention exhibit antitumor activities in in vivo and/or in vitro models. For example, the following test describes the in vivo test used to evaluate some representative compounds of this invention.

Mice M109 Model

Balb/c x DBA/2 $F_1$ hybrid mice were implanted intraperitoneally, as described by William Rose in Evaluation of Madison 109 Lung Carcinoma as a Model for Screening Antitumor Drugs, Cancer Treatment Reports, 65, No. 3–4 (1981), with 0.5 mL of a 2% (w/v) brei of M109 lung carcinoma.

Mice were treated with compounds under study by receiving intraperitoneal injections of various doses on either days 1, 5 and 9 post-tumor implant or days 5 and 8 post-implant. Mice were followed daily for survival until approximately 75–90 days post-tumor implant. One group of mice per experiment remained untreated and served as the control group.

Median survival times of compound-treated (T) mice were compared to the median survival time of the control (C) mice. The ratio of the two values for each compound-treated group of mice was multiplied by 100 and expressed as a percentage (i.e. % T/C) in the following table for representative compounds.

| Compound | % T/C (dose in mg/kg/injection; schedule) |
| --- | --- |
| Ia | 166% (50 mg/kg/inj; days 5 & 8) |
| Ib | 138% (60 mg/kg/inj; days 5 & 8) |

Thus, another aspect of the instant invention concerns a method for inhibiting human and/or other mammalian tumors which comprises administering to a tumor bearing host an antitumor effective amount of a compound of formula I.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mg/m$^2$ over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I, or a pharmaceutically acceptable salt thereof

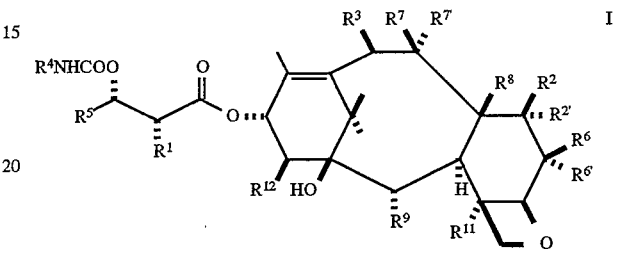

wherein $R^1$ is hydroxy, —OC(O)$R^x$ or —OC(O)O$R^x$; $R^2$ is hydrogen, hydroxy, methoxy, —OC(O)$R^x$ or —OC(O)O$R^x$; $R^{2'}$ is hydrogen, hydroxy or fluoro; $R^{6'}$ is hydrogen or hydroxy; $R^6$ is hydrogen, or $R^2$ and $R^6$ together can form oxirane ring or a bond; $R^3$ is hydrogen, hydroxy, $C_{1-6}$alkyloxy, —OCONR$^{14}$R$^{15}$, —OC(O)$R^x$ or —OC(O)OR$^x$; $R^8$ is methyl or hydroxymethyl, or $R^8$ and $R^2$ together form cyclopropane ring; $R^9$ is hydroxy or —OC(O)$R^x$; with the proviso that when $R^8$ and $R^2$ form cyclopropane ring, $R^{2'}$ is hydrogen; when $R^2$ and $R^6$ form oxirane ring or double bond, $R^{2'}$ and $R^{6'}$ are hydrogen; when $R^2$ is hydroxy, methoxy, —OC(O)$R^x$ or —OC(O)OR$^x$, $R^{2'}$ is hydrogen; when $R^{2'}$ is fluoro, $R^2$ is hydrogen; one of $R^7$ or $R^{7'}$ is hydrogen and the other is hydroxy, —OC(O)$R^x$ or —OC(O)OR$^x$, or $R^7$ and $R^{7'}$ together form an oxo group; $R^{14}$ and $R^{15}$ are independently $C_{1-6}$ alkyl, hydrogen, aryl or substituted aryl; $R^4$ and $R^5$ are independently $C_{1-6}$ alkyl, $C_{2-6}$ alkenyl, $C_{2-6}$ alkynyl, or —Z—$R^{10}$; Z is a direct bond, $C_{1-6}$ alkyl or $C_{2-6}$ alkenyl; $R^{10}$ is aryl, substituted aryl, $C_{3-6}$ cycloalkyl or heteroaryl; $R^{11}$ is —OC(O)$R^y$ or —OC(O)OR$^y$; $R^{12}$ is hydrogen or hydroxy; $R^y$ is $C_{3-6}$ cycloalkyl or $C_{1-6}$ alkyl; $R^x$ is $C_{3-6}$ cycloalkyl, $C_{2-6}$ alkenyl or $C_{1-6}$ alkyl, all are optionally substituted with one to six same or different halogen atoms; or $R^x$ is a radical of the formula

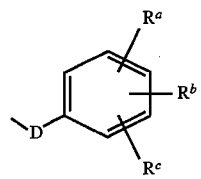

wherein D is a bond or $C_{1-6}$ alkyl; and $R^a$, $R^b$ and $R^c$ are independently hydrogen, nitro, cyano, azido, amino, $C_{1-6}$ alkylamino, di-$C_{1-6}$ alkylamino, halogen, $C_{1-6}$ alkyl, hydroxy or $C_{1-6}$ alkoxy.

2. A compound as claimed claim 1 which has the formula

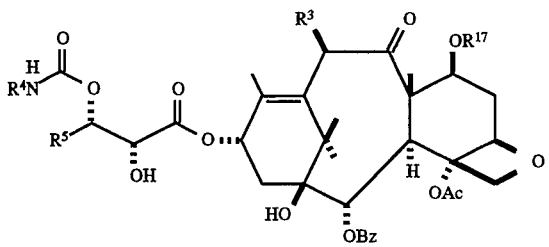

in which $R^{17}$ is methyl or hydrogen; and $R^3$, $R^4$ and $R^5$ are as defined in claim 1.

3. A compound as claimed in claim 2 in which $R^3$ is hydroxy or acetyloxy, $R^4$ is $C_{1-6}$ alkyl or $C_{3-6}$ cycloalkyl, $R^5$ is furyl or phenyl, and $R^{17}$ is hydrogen.

4. A compound as claimed in claim 3 in which $R^3$ is acetyloxy, $R^4$ is t-butyl, and $R^5$ is phenyl.

5. A compound as claimed in claim 3 in which $R^3$ is acetyloxy, $R^4$ is t-butyl, and $R^5$ is 2-furyl.

6. A compound as claimed in claim 3 in which $R^3$ is hydroxy, $R^4$ is t-butyl, and $R^5$ is phenyl.

7. A compound as claimed in claim 3 in which $R^3$ is hydroxy, $R^4$ is t-butyl, and $R^5$ is 2-furyl.

8. A compound as claimed in claim 3 in which $R^3$ is acetyloxy, $R^4$ is isopropyl, and $R^5$ is phenyl.

9. A compound as claimed in claim 3 in which $R^3$ is acetyloxy, $R^4$ is isopropyl, and $R^5$ is 2-furyl.

10. A compound as claimed in claim 3 in which $R^3$ is acetyloxy, $R^4$ is cyclobutyl, and $R^5$ is 2-furyl.

11. A compound as claimed in claim 2 in which $R^3$ is hydroxy or acetyloxy, $R^4$ is $C_{1-6}$ alkyl or $C_{3-6}$ cycloalkyl, and $R^5$ is furyl or phenyl, and $R^{17}$ is methyl.

12. A compound as claimed in claim 11 in which $R^3$ is acetyloxy, $R^4$ is t-butyl, and $R^5$ is 2-furyl.

13. A compound as claimed in claim 11 in which $R^3$ is acetyloxy, $R^4$ is cyclobutyl, and $R^5$ is 2-furyl.

14. A pharmaceutical formulation which comprises an antitumor effective amount of a compound of formula I as claimed in any one of claims 1–13.

15. A method for inhibiting tumor growth in a mammalian host which comprises administering to said mammal a tumor-growth inhibiting amount of a compound of formula I as claimed in any one of claims 1–13.

* * * * *